United States Patent
Burton

(10) Patent No.: US 7,925,887 B2
(45) Date of Patent: Apr. 12, 2011

(54) MULTI-PARAMETER BIOMETRIC AUTHENTICATION

(75) Inventor: David Burton, Camberwell (AU)

(73) Assignee: Intellirad Solutions Pty Ltd. (AU)

(*) Notice: Subject to any disclaimer, the term of this patent is extended or adjusted under 35 U.S.C. 154(b) by 735 days.

(21) Appl. No.: 10/557,186

(22) PCT Filed: May 19, 2004

(86) PCT No.: PCT/AU2004/000664
§ 371 (c)(1),
(2), (4) Date: Mar. 15, 2006

(87) PCT Pub. No.: WO2004/102360
PCT Pub. Date: Nov. 25, 2004

(65) Prior Publication Data
US 2006/0282671 A1  Dec. 14, 2006

(30) Foreign Application Priority Data
May 19, 2003  (AU) ................................ 2003902422

(51) Int. Cl.
*G06F 21/00* (2006.01)
*G06F 7/04* (2006.01)
*G06K 9/00* (2006.01)

(52) U.S. Cl. ............ 713/186; 726/5; 382/115; 340/5.82

(58) Field of Classification Search ...... 726/5; 713/186; 382/115; 340/5.82
See application file for complete search history.

(56) References Cited

U.S. PATENT DOCUMENTS

| | | | |
|---|---|---|---|
| 5,991,408 A | 11/1999 | Pearson et al. | |
| 6,219,639 B1 | 4/2001 | Bakis et al. | |
| 6,256,737 B1* | 7/2001 | Bianco et al. | 713/186 |
| 6,311,272 B1* | 10/2001 | Gressel | 713/186 |
| 6,507,662 B1 | 1/2003 | Brooks | |
| 7,007,298 B1* | 2/2006 | Shinzaki et al. | 726/3 |
| 7,181,048 B2* | 2/2007 | Blume | 382/115 |
| 7,200,753 B1* | 4/2007 | Shinzaki et al. | 713/182 |
| 7,278,028 B1* | 10/2007 | Hingoranee | 713/186 |
| 7,571,315 B1* | 8/2009 | Smith | 713/158 |
| 2003/0115475 A1* | 6/2003 | Russo et al. | 713/186 |
| 2003/0163710 A1* | 8/2003 | Ortiz et al. | 713/186 |
| 2003/0163739 A1* | 8/2003 | Armington et al. | 713/202 |
| 2004/0010697 A1* | 1/2004 | White | 713/186 |
| 2007/0198850 A1* | 8/2007 | Martin et al. | 713/186 |
| 2008/0148059 A1* | 6/2008 | Shapiro | 713/186 |

* cited by examiner

*Primary Examiner* — Techane J Gergiso
(74) *Attorney, Agent, or Firm* — Morgan, Lewis & Bockius LLP

(57) ABSTRACT

Authenticating an identity of a user claiming to be a genuine-user includes receiving from the user biometric data pertaining to a plurality of biometric parameters. The received biometric data are compared with corresponding authentic biometric data which have previously been obtained from the genuine-user. The user's identity is authenticated if the received biometric data meet qualification criteria when compared with the corresponding authentic biometric data.

26 Claims, 3 Drawing Sheets

MULTI-PARAMETER BIOMETRIC AUTHENTICATION

FIELD OF THE INVENTION

The present invention relates to authentication using a plurality of biometric parameters.

BACKGROUND TO THE INVENTION

Security integrity and an assurance have become increasingly important as Internet and world-wide-web usage have become more prevalent and capabilities of these media have grown. The significance of security integrity and assurance has also increased because businesses, government departments, medical organisations and individuals have become somewhat reliant on computer networks and on security of proprietary information transmitted across these networks being of an acceptable level. In an information-driven society it is essential that security systems designed to prevent unauthorised access to information and restricted areas can be relied upon. This challenge is complicated by recent growth in computer and security fraud and code-breaking capacity.

Data transferred across the Internet and other publicly accessible communication networks can be intercepted. It is possible for an unauthorised snoop to intercept data for which they are not the intended recipient. Whilst intercepted data of this kind may be encrypted, it is possible for the data to be analysed if adequate computer power and sufficiently sophisticated code-breaking software is used. Such unauthorised access to data enables snoops to create mischief. However, in many cases, unauthorised access will have more serious consequences.

Fortunately, as computer and identity fraud becomes more sophisticated, so too do security methods and devices which are implemented to combat this fraud. Data encryption is now commonplace and the length of encryption codes is growing in step with processing power available to decipher them. It is now relatively common to use encryption keys having 1024 bits or more. Other security standards such as those deployed by CISCO "roll" encryption codes. That is, data encryption codes are changed dynamically as the data is transferred. This adds a further layer of complexity to the encryption method, thereby reducing the likelihood of an unauthorised security breach occurring.

Recently, use of biometric data has been realised as suitable for verifying the identity of a person requiring access to a restricted area, restricted information, a network intended for restricted use or other such facilities. U.S. Pat. No. 6,016,476 (Maes, et al.) presents a system operating on a PDA in which both voice recognition biometric data and a current certified digital certificate must be present and verified before allowing a transaction to be completed.

A disadvantage of this type of system is that voice biometric data validation is imprecise. Therefore, on some occasions, the system may inadvertently verify users who are not authorised users, enabling them to gain access to a restricted area. A further disadvantage is presented when an attempt at voice biometric data verification is made in a noisy environment. In noisy surrounds, voice biometric data verification is difficult, if not impossible to detect, due to interference caused by ambient and environmental sounds.

European patent EP1263164A1 (Büttiker) presents a portable information and transaction processing system and method utilising biometric authorisation and digital certificate security. EP1263164A1 discloses registration of a public key infrastructure based on credentials which include biometric data. Such biometric data may include data from a subject's fingerprints which is used as input in the security authorisation method. A drawback of this method is that validation of a single biometric parameter suffers problems of reliability because a single biometric validation process can be "cracked" or "fooled" with relative ease. U.S. Pat. No. 6,310,966 B1 (Dulude et al.) which discloses a system in which biometric data is combined with digital certificates for electronic authentication as "biometric certificates" suffers a similar drawback.

It is an object of the present invention to overcome or at least ameliorate one or more of the disadvantages described above.

The discussion of the background to the invention included herein including reference to documents, acts, materials, devices, articles and the like is intended to explain the context of the present invention. This is not to be taken as an admission or a suggestion that any of the material referred to was published, known or part of the common general knowledge in the area as at the priority date of any of the claims.

SUMMARY OF THE INVENTION

According to a first aspect of the present invention, there is provided a method for authenticating identity of a user claiming to be a genuine-user, including the steps of:
(a) receiving from the user biometric data pertaining to a plurality of biometric parameters;
(b) comparing the received biometric data with corresponding authentic biometric data; and
(c) authenticating the user's identity if the received biometric data meet qualification criteria when compared with the corresponding authentic biometric data;
wherein the corresponding authentic biometric data have previously been obtained from the genuine-user.

The plurality of biometric parameters may include visual, acoustic, genetic and/or other biometric parameters. The biometric data may be obtained by determining an eye characteristic, a vocal pattern or characteristic, hand geometry, a facial feature, finger or thumb print or handwriting pattern of the user or even collecting a biological sample from the user. In one embodiment it is desirable that the plurality of biometric parameters includes a biometric parameter of the eye obtained by performing a scan such as a retinal or iris scan or by obtaining an image of the eye and using feature recognition or other suitable software to ascertain another biometric data of the eye such as a blink rate or response, an eye opening or closure characteristic or the like.

In one embodiment, the received biometric data are provided by the user in response to a prompt for required biometric parameters. The required biometric parameters may be determined based on the environment in which the user is being authenticated. Alternatively or additionally, the user may be prompted for required biometric parameters which are randomly selected from a larger set of biometric parameters for which there is corresponding authentic biometric data. Any combination or available biometric data may be used such as eye biometric data relating to the iris and relating to a blink rate response, for example, plus hand geometry, voice pattern or other biometric data.

The qualification criteria may include any suitable rules for authenticating the user. As some biometric data are more precise and have better accuracy than others, the qualification criteria may take into consideration the nature of the biometric data and give one type of biometric data precedence over another when compared with the authentic biometric data for verification. Alternatively, the qualification criteria may require a "substantial match" between all of the received and corresponding authentic biometric data (e.g. a 98% match) to authenticate the user's identity. The criteria may be based on or varied according to the circumstances or environment in which the authentication takes place. Preferably, the qualification criteria are adjustable, based on the biometric parameters for which biometric data is received.

In one preferred embodiment, biometric data pertaining to the plurality of biometric parameters must be received from the user substantially simultaneously. In another embodiment, biometric data pertaining to the plurality of biometric parameters must be received from the user sequentially. In a further alternative biometric data pertaining to three or more biometric parameters may be obtained in a combination of sequential and simultaneous collections.

In one embodiment, each biometric data has an associated qualification factor and the inventive method further includes the step of using the qualification factor associated with each of the received biometric data to determine if the qualification criteria have been satisfied. In one embodiment where the biometric data must be obtained sequentially, the sequence may be pre-defined based on the qualification factor associated with each biometric data to be received.

In a preferred embodiment, a communication device is activated at the completion of the authentication method to provide the user with an indication of his or her authentication status. Such communication device may include an illumination device such as a light emitting diode (LED) or a liquid crystal display (LCD). Preferably illumination occurs in a plurality of colours to provide the user with an intuitive indication of their authentication status.

According to a second aspect of the present invention, there is provided an authentication system for authenticating identity of a user claiming to be a genuine-user, the system including:
(a) biometric data receiving means for receiving from the user biometric data pertaining to a plurality of biometric parameters;
(b) authentic biometric data obtained from the genuine-user;
(c) a processor for comparing the biometric data received from the user with the authentic biometric data; and
(d) authentication status communication means to indicate an authentication status of the user being authenticated;
wherein the user's identity is authenticated if the received biometric data meets qualification criteria when compared with the corresponding authentic biometric data.

The biometric data receiving means may include any suitable scanning or other biometric data obtaining device or a combination of such devices. In one embodiment the biometric data receiving means includes means for obtaining biometric data pertaining to any combination of two or more of a vocal pattern, a voice characteristic, a hand geometry, a facial feature, a finger or thumb print, a handwriting pattern, an eye characteristic, a biological sample or any other biometric data. Any combination of biometric data obtaining means may be used such as an iris scanner and a conductive plate for detecting a finger and/or thumb print and/or a handwriting pattern or signature, for example.

Preferably, the authentic biometric data is stored on a mobile data-storage device. Alternatively, the authentic biometric data may be stored in a remotely accessible secure database.

In one embodiment, the processor may be configured to prompt the user to provide biometric data pertaining to a plurality of required biometric parameters. The processor may be configured to determine the required biometric parameters automatically, based on an environment in which the user is being authenticated. The processor may also be configured to randomly select the required biometric parameters from a larger set of biometric parameters for which there is corresponding authentic biometric data.

Preferably, the processor is configurable to receive different combinations of biometric data and authenticate identity of the user if the qualification criteria are satisfied. In one embodiment, each biometric data has an associated qualification factor and the processor is configured to use the qualification factor associated with each of the received biometric data to determine if the qualification criteria have been satisfied. In such an embodiment, the processor may be configurable to require certain biometric data in a pre-defined sequence which is based on associated qualification factors.

The authentication status communication means may be any suitable means for indicating to the user their authentication status. In one embodiment, this may include use of coloured light emitting diodes (LEDs) where, for example, illumination of a green light indicates that the user's identity has been authenticated and illumination of a red LED indicates that the user's identity has not been authenticated.

According to a third aspect of the present invention, there is provided authentication apparatus for authenticating identity of a user claiming to be a genuine-user, the authentication apparatus including:
(a) biometric data receiving means for receiving biometric data pertaining to a plurality of biometric parameters;
(b) biometric data storage, storing authentic biometric data belonging to the genuine-user;
(c) a processor for comparing received biometric data with corresponding stored authentic biometric data; and
(d) authentication status communication means to indicate an authentication status of the user;
wherein the user's identity is authenticated if the received biometric data meets qualification criteria when compared with the corresponding authentic biometric data.

The biometric data receiving means may include one or more devices suitable for receiving biometric data pertaining to a plurality of different biometric parameters. In one embodiment, the biometric data receiving means includes means for obtaining biometric data pertaining to two or more of a vocal pattern, a voice characteristic, a hand geometry, a facial feature, a finger or thumb print, a handwriting pattern, an eye characteristic and a biological sample or any other biometric data. Any combination of biometric data may be suitable, such as eye biometric data and vocal pattern biometric data and hand geometry biometric data, to give just one example.

It is also desirable that the processor is configurable to receive different combinations of biometric data and determine if the qualification criteria have been satisfied. Preferably, the processor is also configurable to receive biometric data pertaining to a plurality of biometric parameters simultaneously, consecutively and/or in response to a prompt given by the authentication apparatus. In one embodiment, each biometric data has an associated qualification factor and the processor is configurable to use the qualification factor associated with each of the received biometric data to determine if the qualification criteria have been satisfied.

Preferably, the authentication apparatus is a mobile authentication device which may be carried by the user and is suitable for authenticating the user at a number of different locations. Preferably, the biometric data receiving means are small enough to be incorporated into a mobile authentication apparatus such as a smart card type device or a key ring. Preferably, the authentication status communication means includes intuitive indicators. Such indicators may include but are not limited to a light emitting diode (LED), a liquid crystal display (LCD), an audible tone and an audible voice recording.

BRIEF DESCRIPTION OF THE DRAWINGS

The present invention will now be described in greater detail with reference to the accompanying drawings. It is to be understood that the particularity of the accompanying drawings does not supersede the generality of the preceding description of the invention.

DETAILED DESCRIPTION

Figure 1:
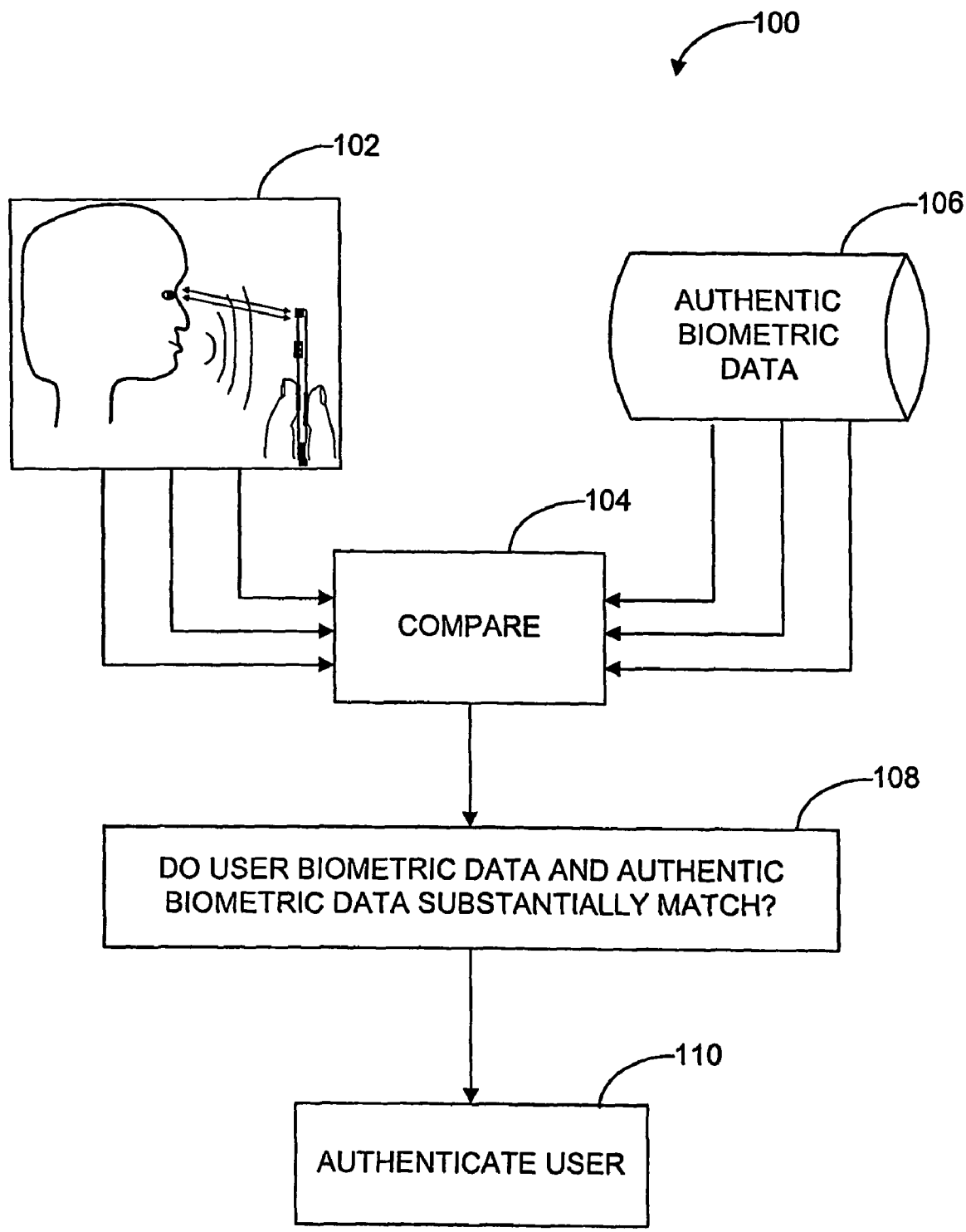
FIG. 1 is a flow diagram illustrating a method embodiment of the present invention.

Referring firstly to FIG. 1, there is provided a flow diagram illustrating a method, generally referred to by reference numeral 100, according to an embodiment of the invention. In a step 102, biometric data pertaining to a plurality of biometric parameters is received from the user. In a step 104, the received biometric data is compared with corresponding authentic biometric data 106 previously obtained from the genuine-user. If, in step 108, the received biometric data substantially match corresponding authentic biometric data, then the user's identity is authenticated in step 110.

Figure 2:
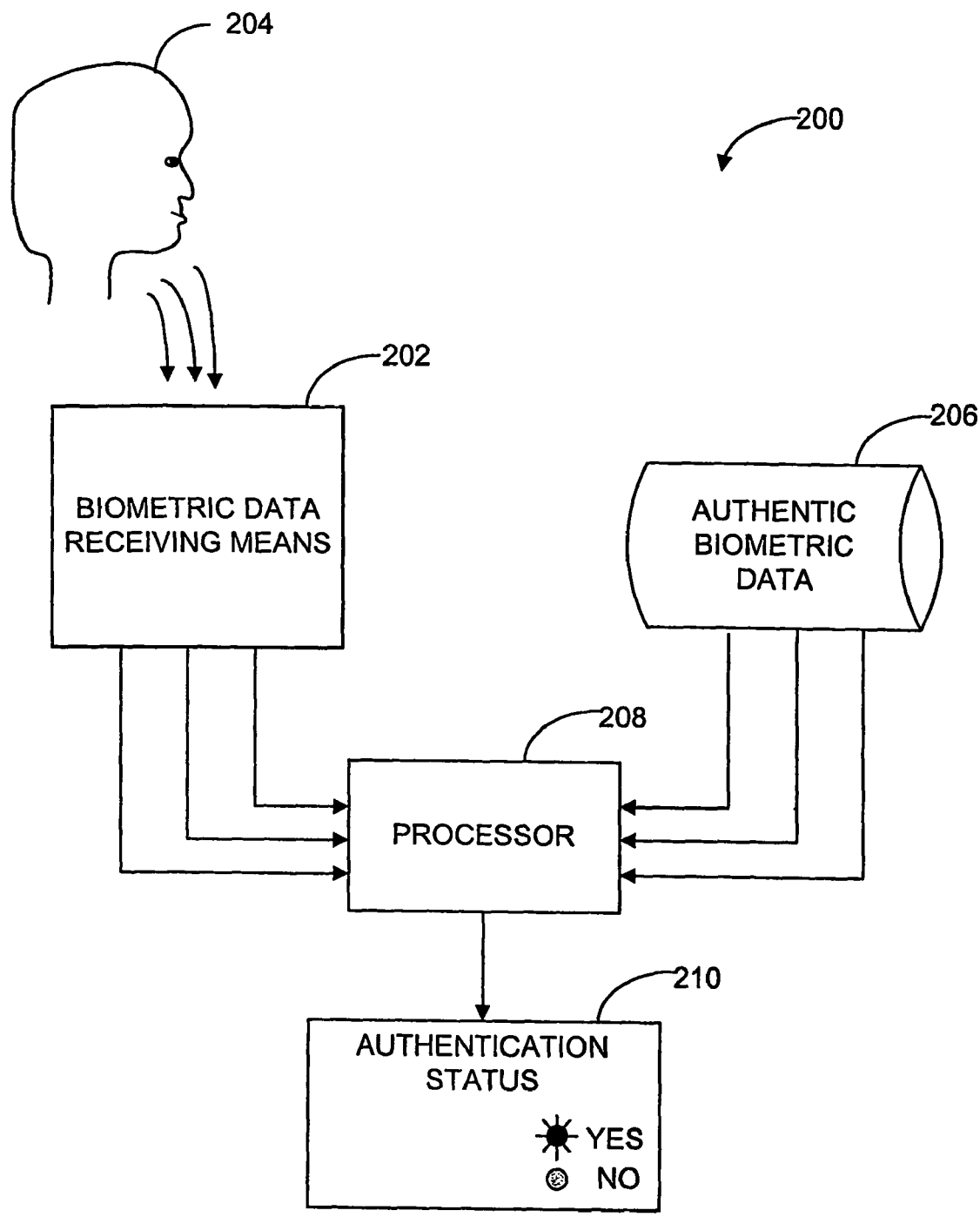
FIG. 2 is a block diagram illustrating a system embodiment of the present invention.

FIG. 2 shows an embodiment of an authentication system generally referred to by reference numeral 200. Biometric data receiving means 202 receives biometric data from user 204 pertaining to a plurality of biometric parameters. The biometric data may relate to acoustic, visual, genetic or other biometric parameters of the user. Authentic biometric data 206 previously obtained from the genuine-user is compared with biometric data received from the user 204 using processor 208. Authentication status communication means 210 then provides an indication of the user's authentication status to indicate that the user's identity has been authenticated as the genuine-user, or invalidated.

Biometric data receiving means 202 is configured to receive input from two or more biometric input data sets simultaneously or consecutively. For three or more biometric data, the data may be received using a combination of simultaneous and consecutive processes. In one embodiment, received biometric data includes biometric data resulting from an eye scan and one or more other biometric parameters. Retinal or iris biometric data may be determined by a scan of the eye. Retinal scans require the biometric data receiving means (scanner) 202 to be located very close to the user's eye, and in most cases this is achieved by coupling a cup-like apparatus over the eye. This can be uncomfortable and intrusive from the user's perspective. Scans of the iris are generally less intrusive as the user is not required to be uncomfortably close to a camera obtaining an image of the eye for verification of the biometric data and so may therefore be more desirable.

Additionally or alternatively, the eye scan may be used to obtain an angle of reflective eye tracking. In such embodiment, to obtain this angle, a subject's eye may be illuminated with a near-infrared LED while a camera collects images of the eyes. The processor can then calculate the position of the centre of the pupil and the reflective light on the eye. Additionally or alternatively, biometric data relating to the eye may include a subtraction signal obtained by determining a difference between two scans of the eye taken at two predetermined angles or levels. Such biometric data can be verified by comparison with a corresponding subtraction signal previously obtained from the genuine-user using the same scan angles or levels.

The biometric data obtaining means may also be configured to detect a reflected infrared or other light directed into and reflected by the user's iris in accordance with the user's iris characteristics. A precise composition of the light reflected from the iris may allude to a specific iris behaviour and response unique to the user. Alternatively or additionally, a video camera and processor may be used to detect blink and closure characteristics of one or both of the user's eyes. Any combination of the user's blink velocity, blink response, eye opening and/or closure characteristics, iris characteristics and other eye specific data could be combined in this manner to produce a unique eye biometric data combination or "foot print" unique to the user. As another alternative, video recognition may be used whereby consecutive frames are compared and provide information on blinks or eye closure changes, for example.

One or more cameras can also be used to obtain one or more video images for use by recognition software to compare one or more distinctive facial or other characteristics of the user with corresponding distinctive characteristics of the genuine-user for verification/authentication. Examples of such characteristics include but are not limited to head size and/or shape, nose size and/or shape, chin shape and other facial features.

Other biometric data received may require detection of any combination of a vocal pattern, a voice code sequence or voice sound characteristics of the user, detection of the user's hand geometry, detection of a facial feature of the user, detection of a finger or thumb print of the user, or detection of the user's signature or other handwriting pattern. As an alternative, and as DNA and genetic technologies become more sophisticated, faster and more accessible, it is possible that skin, saliva, blood or another biological sample may be obtained from the user to provide one form of biometric data.

In a preferred embodiment, processor 208 is configured to give a prompt, inviting the user to provide biometric data pertaining to a plurality of required biometric parameters. In one such embodiment the processor may be configured to determine the nature of the required biometric parameters automatically, based on an environment in which the user is being authenticated. For example, when the environment is a public environment such as a library or shopping centre, the processor 208 may be configured to prompt the user 204 to provide required biometric data which are less likely to jeopardise security (i.e. be detected and copied by others) in that environment. Such biometric data may relate to one or more of retinal parameters, iris parameters, hand geometry, a facial feature characteristic or a finger or thumb print. Alternatively, when the environment in which the user's identity is being authenticated is a secure environment such as a secure room or the user's own home, the processor 208 may be configured to prompt the user 204 to provide required biometric data which may be less secure, such as voice pattern biometric data or a handwriting sample such as a signature.

In one embodiment, it is preferred that the user is required to provide the plurality of biometric data substantially simultaneously in order for the authentication to take place. This reduces the likelihood of a false authentication occurring because of the difficulty of falsifying a plurality of biometric data simultaneously. Alternatively, it may be necessary for the user to provide the biometric data in a pre-defined sequence. A combination of simultaneous and consecutive inputs may also be required, to improve the security of the authentication process and effectiveness of the system. To further improve the accuracy of the system, the processor may be configured to prompt the user for required biometric parameters which are randomly selected from a larger set of biometric parameters for which there is corresponding authentic biometric data. This may further reduce the likelihood of a fraudulent user being falsely authenticated as the genuine user.

Each of the biometric data also have a qualification factor, based on the accuracy and/or reliability of the biometric data type and/or obtaining means (e.g. scanner). This qualification factor is incorporated into the qualification criteria which ultimately determines if the user's identity is authenticated. Preferably, the qualification criteria are adjustable by an administrator or security access manager. For example, qualification criteria may be determined based on a security rating allocated to a restricted area or information set.

Alternatively or additionally, the processor may be configured to adjust the qualification criteria automatically, based on, say, the biometric data which is received from the user. In such an embodiment, if high accuracy biometric data such as an iris scan is received is a 98% match with that of the genuine-user, the qualification criteria may only require verification of one further biometric data to authenticate the user's identity, whereas after receipt of signature biometric data, which is less reliable, the qualification criteria may require 2, 3 or 4 more forms of biometric data to be provided and verified before the user's identity can be authenticated. It is also desirable for the processor to be configurable to require the biometric data in a particular pre-defined sequence, based on a qualification factor associated with each of the biometric data.

Figure 3:
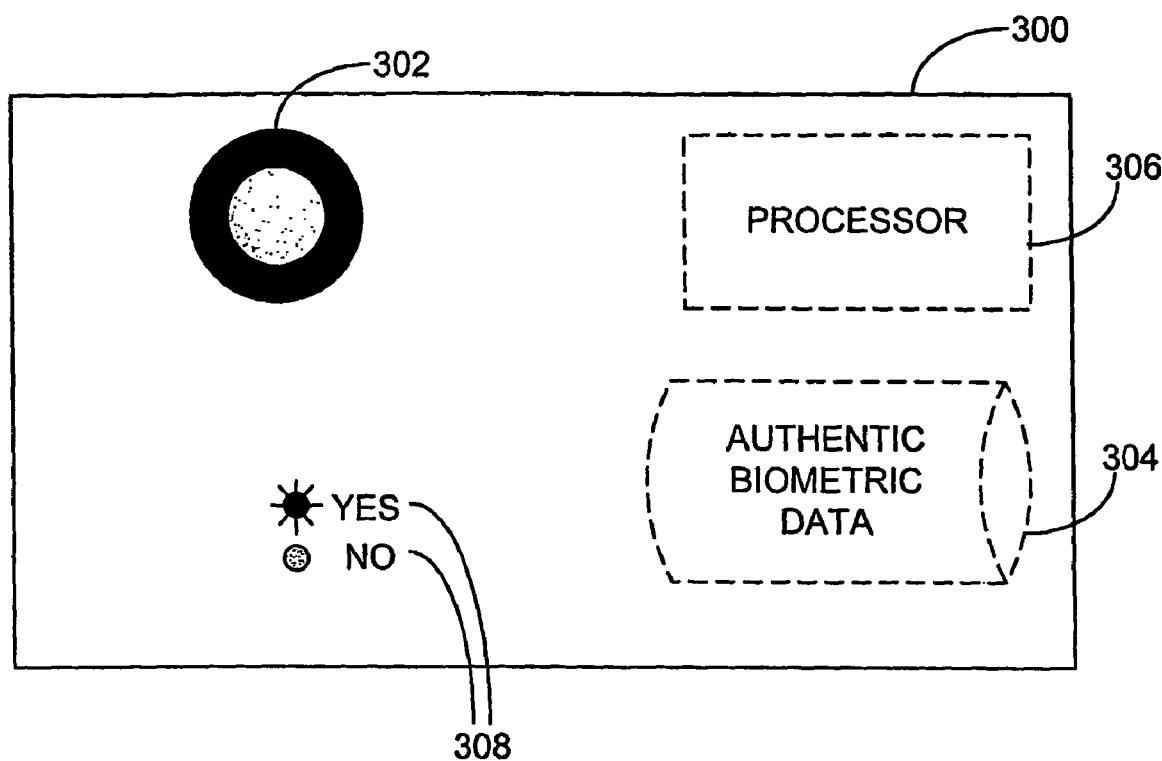
FIG. 3 is an illustration of an apparatus embodiment of the present invention.

FIG. 3 illustrates an embodiment of an authentication apparatus generally referred to by 300, according to an embodiment of the invention. Authentication apparatus 300 includes biometric data receiving means 302 provided in the form of an eye scan camera. The camera may be configured to perform iris scans to determine biometric data for the user's left and right eyes separately, thereby obtaining two separate biometric inputs for use in verifying the user's identity. Biometric data storage 304 stores authenticated biometric data belonging to and obtained from the genuine-user.

Processor 306 processes the received biometric data and compares it with corresponding authentic biometric data 304 to authenticate the identity of the user as the genuine user, or invalidate the user's identity. Authentication status communication means 308 are provided in the form one or more light emitting diodes (LEDs) or other suitable illumination means. LED 308 is illuminated in the colour green if the user's identity is authenticated and red if the user's identity is not authenticated. It may also be desirable to include a third amber LED which illuminates if verification cannot be completed, if there is an error, or to prompt the user to provide the biometric data a first or a second time. It is to be understood that other authentication status communication means may be provided in addition to or as an alternative to LEDs, such as audible tones and voice recordings.

Other features may be incorporated into the inventive system and apparatus such as a log identifying unsuccessful authentication attempts, and/or the times and locations at which successful authentications have taken place.

It is to be understood that any combination of biometric data may be obtained to authenticate the user's identity as that of the genuine-user and that the higher the number of data verified, the more reliable the authentication. For example, in addition to the camera 302 obtaining biometric data for the left eye and the right eye, there may be included a conductive pad to receive biometric data corresponding to the user's signature or other handwriting pattern or a finger or thumb print.

It is desirable that the biometric data receiving means is small enough to fit onto a mobile device such as a smart card, key ring or other such device which can be carried by the user and used to authenticate the user's identity to allow access to different areas and information in various locations. It also enables the authentication apparatus to be locked away adding a further level of security. However, it is to be understood that as an alternative, parts of the authentication system such as the authentic biometric data may be accessible over a network, where it is not necessary for the authentic biometric data to be stored on a device held by the user, although the latter may be preferable for privacy purposes.

Preferably, the apparatus is programmable to receive different biometric data types in different processes, e.g. simultaneously, consecutively or a combination of these. The apparatus may also be programmable to require different biometric data, depending on the environment or access level for which it is being used. Once the user's identity has been validated, the apparatus 300 may then send by way of radio transmission or wired computer interface, an unlock encryption key or other code to a remote device to gain access to protected information or a restricted area The present invention uses multiple forms of biometric data for simultaneous or sequential verification to authenticate the identity of a user as a genuine-user. In doing so, it increases a level of security assurance which can be provided when the user is accessing restricted areas or information. The present invention further enhances the security access level by providing an optional means to accept either simultaneously or consecutively biometric data, such as a user's biometric eye data, voice, facial features, hand geometry, handwriting pattern, biological sample or other suitable biometric data and rate that data based on associated qualification factors.

It is to be understood that various modifications, additions and/or alterations may be made to the parts previously described without departing from the ambit of the present invention as defined in the claims appended hereto.

The invention claimed is:

1. A processor-implemented method for authenticating an identity of a user claiming to be a genuine-user, the method being executed on a authentication processing apparatus, including the steps of:
   (a) receiving biometric data from the user of the authentication processing apparatus, said biometric data pertaining to a plurality of biometric parameters; and
   (b) comparing the received biometric data with a corresponding authentic biometric data pre-determined based on the authentication environment and authenticating the user's identity using the processor according to physical authentication environment and circumstances;
   wherein the received biometric data is required to meet qualification criteria prior to comparing, and wherein the corresponding authentic biometric data were received previously from the genuine-user;
   wherein the authentication environment is selected from a public environment or a private environment;
   wherein more than one biometric data are received simultaneously from the user in a pre-defined sequence, the pre-defined sequence comprising: a simultaneous sequence or a consecutive sequence;
   wherein the plurality of biometric parameters are selected from two or more of: (a) a visual biometric parameter of the user; (b) an acoustic biometric parameter of the user; or (c) a genetic biometric parameter of the user; and wherein the received biometric data comprises biometric data resulting from detection of a combination of two or more of: (a) a vocal pattern; (b) a voice characteristic; (c) a hand geometry; (d) a facial feature; (e) a finger or thumb print; (f) a handwriting pattern; (g) an eye characteristic; or (h) a collection of a biological sample.

2. The method of claim 1, wherein the received biometric data comprises biometric data resulting from detection of an eye characteristic and one or more of:
   (a) a vocal pattern;
   (b) hand geometry;
   (c) a facial feature;
   (d) a finger or thumb print:
   (e) a handwriting pattern; or
   (f) a collection of a biological sample.

3. The method of claim 1, wherein the received biometric data comprises biometric data resulting from detection of a hand geometry, a vocal pattern and one or more of:
   (a) an eye characteristic;
   (b) a facial feature;
   (c) a finger or thumb print;
   (d) a handwriting pattern; or
   (e) a collection of a biological sample.

4. The processor-implemented method for authenticating the identity of a user according to claim 1, wherein the received biometric data comprises biometric data resulting from detection of an eye characteristic and a hand geometry and one or more of:
   (a) a vocal pattern;
   (b) a facial feature;
   (c) a finger or thumb print;
   (d) a handwriting pattern; or
   (e) a collection of a biological sample.

5. The method of claim 1, wherein the eye characteristic comprises one or more of the following:
   (a) an iris response behavior;
   (b) an iris response time;
   (c) an iris coloring;
   (d) a blink rate;
   (e) a blink response;
   (f) an eye closure characteristic;
   (g) eye opening characteristic; or
   (h) an angle of reflective eye tracking.

6. The method of claim 1, wherein the received biometric data are provided by the user in response to a prompt for required biometric parameters.

7. The method of claim 1, wherein each parameter of the plurality of biometric data has an associated qualification criteria factor.

8. The method of claim 7, wherein the pre-defined sequence is based on the qualification criteria factor associated with each parameter of the biometric data.

9. The method of claim 1, wherein the qualification criteria are adjustable.

10. The method of claim 1, further comprising activating a communication device to provide the user with an indication of authentication status.

11. The method of claim 10, wherein the communication device includes illumination means that are illuminated in one or more colors to provide an indication of the authentication status.

12. An authentication processing device for executing computer instructions to authenticate an identity of a user claiming to be a genuine-user, the device comprising:

(a) a biometric data receiving device for receiving from the user biometric data pertaining to a plurality of required biometric parameters pre-determined based on an authentication environment for authenticating the user's identity according to physical authentication environment and circumstances;
   (b) authentic biometric data received from the genuine user;
   (c) a microprocessor for executing instructions to compare the received biometric data with the authentic biometric data; and
   (d) an authentication status communication means to indicate an authentication status of the user being authenticated;

wherein the user's identity is authenticated according to whether the received biometric data meets qualification criteria when compared with the corresponding authentic biometric data;

wherein the authentication environment is selected from a public environment or a private environment;

wherein more than one biometric data are received simultaneously from the user in a pre-defined sequence, the pre-defined sequence comprising: a simultaneous sequence or a consecutive sequence;

wherein the plurality of biometric parameters are selected from two or more of: (a) a visual biometric parameter of the user; (b) an acoustic biometric parameter of the user; or (c) a genetic biometric parameter of the user; and wherein the received biometric data comprises biometric data resulting from detection of a combination of two or more of: (a) a vocal pattern; (b) a voice characteristic; (c) a hand geometry; (d) a facial feature; (e) a finger or thumb print; (f) a handwriting pattern; (g) an eye characteristic; or (h) a collection of a biological sample.

13. The device of claim 12, wherein the biometric data receiving means comprises a means for obtaining biometric data pertaining to an eye characteristic and a means for obtaining biometric data pertaining to one or more of the following:
   (a) a vocal pattern;
   (b) a voice characteristic;
   (c) a hand geometry;
   (d) a facial feature;
   (e) a finger or thumb print;
   (f) a handwriting pattern; or
   (g) a biological sample.

14. The device of claim 12, wherein the authentic biometric data is stored on a mobile data-storage device.

15. The device of claim 12, wherein the authentic biometric data is stored in a remotely accessible secure database.

16. The device of claim 12, wherein the processor is configured to prompt the user to provide biometric data pertaining to the plurality of required biometric parameters.

17. The device of claim 12, wherein each parameter of the required biometric data has an associated qualification criteria factor, and the processor is configured to use the qualification criteria factor associated with each parameter of the received biometric data to determine if the qualification criteria have been satisfied.

18. The device of claim 17, wherein the processor is configured to receive different combinations of biometric data and to authenticate the identity of the user if the qualification criteria are satisfied.

19. The method of claim 18, wherein the processor is configured to require specific parameters of the biometric data in a pre-defined sequence, based on the associated qualification factors.

20. An authentication processing device for executing computer instructions to authenticate an identity of a user claiming to be a genuine-user, the device comprising:
- (a) a biometric data receiving device for receiving biometric data pertaining to a plurality of biometric parameters pre-determined based on an authentication environment for authenticating the user's identity according to physical authentication environment and circumstances;
- (b) biometric data storage for storing authentic biometric data belonging to the genuine-user;
- (c) a microprocessor for executing instructions to compare received biometric data with the corresponding authentic biometric data; and
- (d) authentication status communication means to indicate an authentication status of the user;
- wherein the user's identity is authenticated according to if the received biometric data meets qualification criteria when compared with the corresponding authentic biometric data;
- wherein the authentication environment is selected from a public environment or a private environment;
- wherein more than one biometric data are received simultaneously from the user in a pre-defined sequence, the pre-defined sequence comprising: a simultaneous sequence or a consecutive sequence;
- wherein the plurality of biometric parameters are selected from two or more of: (a) a visual biometric parameter of the user; (b) an acoustic biometric parameter of the user; or (c) a genetic biometric parameter of the user; and
- wherein the received biometric data comprises biometric data resulting from detection of a combination of two or more of: (a) a vocal pattern; (b) a voice characteristic; (c) a hand geometry; (d) a facial feature; (e) a finger or thumb print; (f) a handwriting pattern; (g) an eve characteristic; or (h) a collection of a biological sample.

21. The device of claim 20, wherein the biometric data receiving means comprises a means for obtaining biometric data pertaining to the eye and a means for obtaining biometric data pertaining to one or more of the following:
- (a) a vocal pattern;
- (b) a voice characteristic;
- (c) a hand geometry;
- (d) a facial feature;
- (e) a finger or thumb print;
- (f) a handwriting pattern;
- (g) an eye characteristic; or
- (h) a biological sample.

22. The device of claim 20, wherein the device is a mobile device.

23. The device of claim 20, wherein each parameter of the biometric data has an associated qualification criteria factor and the processor is configured to use the qualification criteria factor associated with each of the received biometric data to determine if the qualification criteria were satisfied.

24. The device of claim 20, wherein the processor is configured to determine if the qualification criteria of the more than one biometric data received have been satisfied.

25. The device of claim 20, wherein the authentication status communication means comprises indicators of one or more of the following:
- (a) a light emitting diode (LED);
- (b) a liquid crystal display (LCD);
- (c) an audible tone; or
- (d) an audible voice recording.

26. The method of claim 7, further comprising using the qualification criteria factors associated with each of the received biometric data to determine if the qualification criteria were satisfied.

* * * * *